United States Patent
Hashimoto et al.

(10) Patent No.: US 8,431,606 B2
(45) Date of Patent: Apr. 30, 2013

(54) MEDICAMENT FOR TREATING SCHIZOPHRENIA COMPRISING CILOSTAZOL

(75) Inventors: Kenji Hashimoto, Chiba (JP); Masaomi Iyo, Chiba (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 477 days.

(21) Appl. No.: 12/593,886

(22) PCT Filed: Mar. 28, 2008

(86) PCT No.: PCT/JP2008/056724
§ 371 (c)(1),
(2), (4) Date: Jan. 15, 2010

(87) PCT Pub. No.: WO2008/123592
PCT Pub. Date: Oct. 16, 2008

(65) Prior Publication Data
US 2010/0152247 A1    Jun. 17, 2010

(30) Foreign Application Priority Data

Mar. 30, 2007   (JP) .................. 2007-092596

(51) Int. Cl.
*A61K 31/4439* (2006.01)
*A61K 31/4162* (2006.01)
*C07D 401/12* (2006.01)
*A61P 25/18* (2006.01)

(52) U.S. Cl.
USPC .................. 514/381; 514/340; 546/268.4

(58) Field of Classification Search .......... 514/340, 514/381; 546/268.4
See application file for complete search history.

(56) References Cited

U.S. PATENT DOCUMENTS

| | | | |
|---|---|---|---|
| 6,458,804 | B1 | 10/2002 | Cutler et al. |
| 2003/0130311 | A1 | 7/2003 | Cutler et al. |
| 2006/0034847 | A1 | 2/2006 | Yun et al. |

FOREIGN PATENT DOCUMENTS

| | | |
|---|---|---|
| CN | 1562018 A | 1/2005 |
| EP | 0 367 141 | 5/1990 |
| EP | 1 712 225 A1 | 10/2006 |
| WO | WO 02/14283 A1 | 2/2002 |
| WO | WO-02/060423 A1 | 8/2002 |
| WO | WO-2004/075897 A1 | 9/2004 |

OTHER PUBLICATIONS

Office Action dated Dec. 22, 2010 issued in corresponding Chinese Application No. 200880018289.2.
State Intellectual Property Office, P.R. China, First Office Action and Search Report, Jul. 18, 2012, 7 pages, Beijing, China.
Jeon, Y.H. et al., "Phosphodiesterase: Overview of Protein Structures, Potential Therapeutic Applications and Recent Progress in Drug Development," CMLS, Cellular and Molecular Life Sciences 62 (2005) 1198-1220.

*Primary Examiner* — Shengjun Wang
*Assistant Examiner* — Sahar Javanmard
(74) *Attorney, Agent, or Firm* — Finnegan, Henderson, Farabow, Garrett & Dunner, L.L.P.

(57) ABSTRACT

The invention relates to a medicament for preventing and/or treating schizophrenia which comprises as an active ingredient cilostazol or a pharmaceutically acceptable salt thereof.

2 Claims, 3 Drawing Sheets

MEDICAMENT FOR TREATING SCHIZOPHRENIA COMPRISING CILOSTAZOL

TECHNICAL FIELD

The invention relates to a medicament for preventing and/or treating schizophrenia. More particularly, it relates to a medicament for preventing and/or treating schizophrenia which comprises as an active ingredient a carbostyril derivative of formula (1):

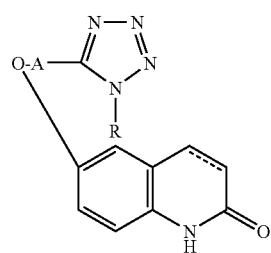

wherein A is a lower alkylene group, R is a cycloalkyl group, the bonding between 3- and 4-positions of the carbostyril skeleton is a single bond or a double bond, or a salt thereof.

BACKGROUND ART

The carbostyril derivatives (1) of formula (1) or salts thereof and the process for the preparation thereof are disclosed in JP-63-20235-B and JP-55-35019-A. And it is known that the carbostyril derivatives (1) have platelet aggregation inhibition action, phosphodiesterase (PDE) inhibition action, antiulcer, hypotensive action and antiphlogistic action, and are useful as an antithrombotic agent, a drug for improving cerebral circulation, an antiinflammatory agent, an antiulcer drug, an antihypertensive drug, an antiasthmatic drug, a phosphodiesterase inhibitor, etc. In addition, JP-2006-518732-A (PTEN INHIBITOR OR MAXI-K CHANNELS OPENER) discloses that the carbostyril derivatives (1) are useful as a medicament for treating anxiety, depression, etc.

Schizophrenia mainly affects people at the period of puberty or adolescence, which is basically caused by disturbance of ego, thought disorder, etc. And schizophrenia is categorized as a chronic psychiatric disorder which gradually becomes severe as positive symptom including hallucination and delusion arises repeatedly.

With the change of social lifestyle and the advance of aging of society, the number of patients suffering from neuropsychiatric disease tends to increase on the whole. For example, schizophrenia is apt to affect about 1% of all the population without the relation to races or areas, which is a neuropsychiatric disease mainly affecting people at the young period from puberty to their twenties. The hospitalized patients suffering from schizophrenia occupy about 15% of the total beds of hospitals in Japan, hence the disease is a big social problem from the viewpoint of medical economy. The conditions of schizophrenia include a positive symptom such as hallucination and delusion, and a negative symptom such as apathy, hypobulia and social withdrawal. The treatment of schizophrenia requires appropriate medicaments, which include phenothiazines, butyrophenones, benzamide compounds, iminodibenzyl compounds, thiepins, indole compounds and serotonin/dopamine receptor blockers as a conventional treatment drug. However, a novel and more effective medicament for treating schizophrenia is still desired in Japan and other countries since the current medicaments are not sufficiently effective.

DISCLOSURE OF INVENTION

Thus, although some medicaments for treating schizophrenia are clinically used as mentioned above, a more effective medicament for treating schizophrenia has been still desired in Japan and other countries since the current medicaments are not sufficiently effective.

The present inventors have intensively studied a new medicament for preventing and/or treating schizophrenia and have found that a carbostyril derivative of the above formula (1), especially 6-[4-(1-cyclohexyl-1H-tetrazol-5-yl)butoxy]3,4-dihydrocarbostyril (cilostazol) or a salt thereof is useful for preventing and/or treating schizophrenia.

Many studies indicate that the impairment of glutamate neurotransmission via N-methyl-D-aspartate (NMDA) receptor is concerned in the pathologies of schizophrenia (Javitt and Zukin, 1991; Olney and Farber, 1995; Hashimoto et al, 2004). NMDA receptor antagonists such as phencyclidine (PCP) are used to prepare model animals suffering form schizophrenia since it is known that NMDA receptor antagonists such as phencyclidine might cause cognitive impairment and schizophrenia syndrome including a negative symptom to healthy subjects.

The present inventors have found on the first time that 6-[4-(1-cyclohexyl-1H-tetrazol-5-yl)butoxy]3,4-dihydrocarbostyril (cilostazol) or a salt thereof could improve the condition of schizophrenia in prevention and/or treatment of schizophrenia on model animals prepared with phencyclidine.

The present invention provides a medicament for preventing and/or treating schizophrenia comprising as an active ingredient a carbostyril derivative of the general formula:

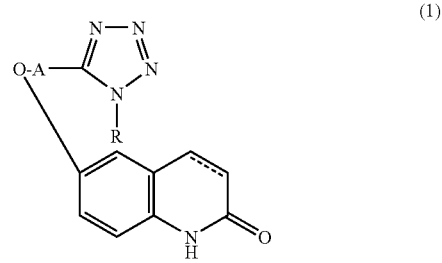

wherein A is a lower alkylene group, R is a cycloalkyl group, the bonding between 3- and 4-positions of the carbostyril skeleton is a single bond or a double bond, or a salt thereof.

The present invention also provides a medicament for preventing and/or treating schizophrenia comprising as an active ingredient 6-[4-(1-cyclohexyl-1H-tetrazol-5-yl)butoxy]3,4-dihydrocarbostyril (cilostazol) or a salt thereof.

The present invention also provides a composition for preventing and/or treating schizophrenia comprising the above-mentioned ingredient.

The present invention also provides use of the above-mentioned ingredient in preparation of a medicament for preventing and/or treating schizophrenia.

The present invention also provides a method for preventing and/or treating schizophrenia which comprises administering an effective amount of the above-mentioned ingredient to a patient in need thereof.

BEST MODE FOR CARRYING OUT THE INVENTION

Figure 1:
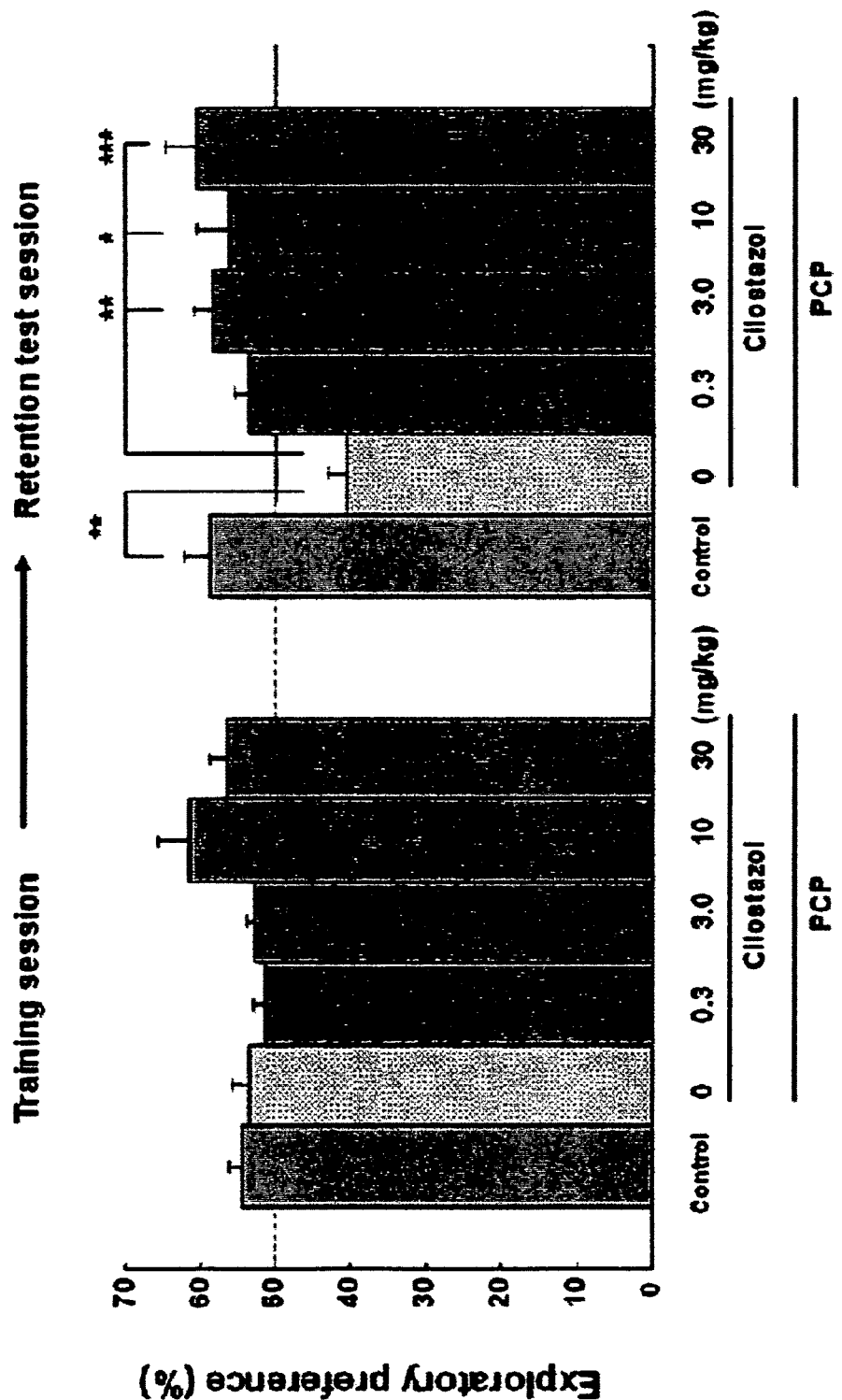
FIG. 1 shows the effects of cilostazol on schizophrenia using model animals prepared with phencyclidine which are one of models for schizophrenia.

In the above carbostyril derivative (1), the cycloalkyl group includes $C_3$-$C_8$ cycloalkyl groups such as cyclopropyl, cyclobutyl, cyclopentyl, cyclohexyl, cycloheptyl, and cyclooctyl. Preferred cycloalkyl group is cyclohexyl. The lower alkylene group includes $C_1$-$C_6$ alkylene groups such as methylene, ethylene, propylene, butylene, and pentylene, among which preferred one is butylene.

Preferable carbostyril derivative (1) is 6-[4-(1-cyclohexyl-1H-tetrazol-5-yl)butoxy]-3,4-dihydrocarbostyril, which has been put on the market in the trade name of cilostazol as an antiplatelet agent.

The carbostyril derivative (1) can be easily converted to a salt thereof by getting it treated with a pharmaceutically acceptable acid. The acid includes, for example, inorganic acids such as hydrochloric acid, sulfuric acid, phosphoric acid, and hydrobromic acid; and organic acids such as oxalic acid, maleic acid, fumaric acid, malic acid, tartaric acid, citric acid, and benzoic acid.

These carbostyril derivatives (1) and salts thereof and processes for preparation thereof are disclosed in JP-55-35019-A (relevant to U.S. Pat. No. 4,277,479).

The carbostyril derivatives (1) of formula (1) may be used in bulk or preferably in the form of a pharmaceutical preparation with a conventional pharmaceutical carrier or diluent. The dosage form in the present invention includes, but not limited thereto, for example, the dosage forms exemplified in JP-2006-518732-A and JP-10-175864-A, and typically an oral solid dosage form such as tablets, capsules, and particles; various liquid preparations suitable for oral administration; and also a parenteral preparations such as injections and suppositories. The dose of the carbostyril derivative (1) is not limited to a specific range. The carbostyril derivatives (1) or a salt thereof may be used in an amount of 100 to 400 mg/day per an adult (50 kg of body weight), which is administered once a day or two to several times per day. The carbostyril derivative (1) may be included in 0.1-70% (w/w) per the composition of the preparation, preferably 50-100 mg per a dosage unit of the preparation.

The preparation for injection is usually prepared in the form of a liquid preparation, an emulsion, or a suspension, which are sterilized and further are preferably made isotonic to the blood. The preparations in the form of liquid, emulsion or suspension are usually prepared by using conventional pharmaceutical diluents such as water, ethyl alcohol, propylene glycol, ethoxylated isostearyl alcohol, polyoxylated isostearyl alcohol, and polyoxyethylene sorbitan fatty acid esters. These preparations may be prepared by mixing the carbostyril derivative (1) with an isotonic agent such as sodium chloride, glucose, glycerin in an amount sufficient for making isotonic and may further be prepared by mixing with conventional solubilizers, buffers, anesthetizing agents, and optionally colorants, preservatives, fragrant materials, flavors, sweetening agents, and other medicaments.

The preparations of the invention such as tablets, capsules, liquid for oral administration may be prepared by a conventional method. The tablets may be prepared by mixing the carbostyril derivative (1) with conventional pharmaceutical carriers such as gelatin, starches, lactose, magnesium stearate, talc, gum arabic, and the like. The capsules may be prepared by mixing the carbostyril derivative (1) with inert pharmaceutical fillers or diluents and filling hard gelatin capsules or soft capsules with the mixture. The oral liquid preparations such as syrups or elixirs are prepared by mixing the carbostyril derivative (1) with sweetening agents (e.g. sucrose), preservatives (e.g. methylparaben, propylparaben), colorants, flavors, and the like. The preparations for parenteral administration may also be prepared by a conventional method, for example, by dissolving the carbostyril derivative (1) of the present invention in a sterilized aqueous carrier, preferably water or a saline solution. Preferred liquid preparation suitable for parenteral administration is prepared by dissolving about 50-100 mg of the carbostyril derivative (1) in water and an organic solvent and further in a polyethylene glycol having a molecular weight of 300 to 5000, in which preferably a lubricant such as sodium carboxymethylcellulose, methylcellulose, polyvinylpyrrolidone, and polyvinyl alcohol may be incorporated. Preferably, the above liquid preparations may further comprise a disinfectant (e.g. benzyl alcohol, phenol, thimerosal), a fungicide, and further optionally an isotonic agent (e.g. sucrose, sodium chloride), a topical anesthetic, a stabilizer, a buffer, and the like. In view of keeping stability, the preparation for parenteral administration may be put in a capsule, followed by removing the aqueous medium by a conventional lyophilizing technique. The preparation can be recovered into a liquid preparation by dissolving it in an aqueous medium when used.

EXAMPLE

Hereinafter, the present invention is further illustrated by the following examples, but should not be construed to be limited thereto. The experimental procedure of the following example was carried out according to the method of Hashimoto, et al. (Eur J Pharmacol. 2006 Dec. 28; 553 (1-3): 191-5, Neuropsychopharmacology. 2007 March; 32(3): 514-21, Eur J. Pharmacol. 2005 Sep. 5; 519 (1-2): 114-7). In addition, it is possible to be variously modified within the range of the technical idea of the invention.

Example 1

(1) Experimental Procedure

Male ICR mice (6 weeks old, 25-30 g, purchased from Japan SLC, Inc.) were used as experimental animals. The experimental procedure was approved by the laboratory animal ethics committee in the Graduate School of Medicine and School of Medicine, Chiba University. Phencyclidine was subcutaneously administered to the mice in 10 mg/kg once a day for 10 days. Three days after the final administration of phencyclidine, the solvent or cilostazol (0.3, 1.0, 3.0, 10 mg/kg) was started to be orally administered to the mice once a day for two weeks.

Twenty four hours after the final administration, re-recognizing test for a new object was carried out. The re-recognizing test for a new object was carried out using a black open-field (50.8×50.8×25.4 cm). The mice were made to be trained in the open-field for three days before starting the re-recognizing test for a new object. Two objects which have almost the same size but different shapes and colors were set separating off in a distance of 35.5 cm, and then the mice were made to seek for 10 minutes. After the seeking, the mice were put back to the gauge. Twenty four hours after the first seeking, a memory retention test was carried out. On this memory retention test, one of the objects was replaced by a new one. The mice were made to seek for 5 minutes, and the time which was taken to seek each object was recorded. The results were shown as a ratio of the seeking time of the new object against that of the two objects.

(2) Statistical Analysis

The data were shown as mean±standard deviation. The statistical analyses thereof were carried out using one-way ANOVA and post-hoc Bonferroni test. A p-value of 0.05 or less was considered as a statistical significance.

(3) Result

The mice which took continuous 10-day administration of phencyclidine (10 mg/kg, subcutaneously) came to significantly decrease their curiosity about the new object (ratio of the seeking time), and thereby it was confirmed that phencyclidine could cause schizophrenia. The condition of schizophrenia caused by phencyclidine was improved through continuous 2-week administration of cilostazol dose-dependently, especially improved significantly in the doses of 3 mg/kg, 10 mg/kg and 30 mg/kg.

From the above-mentioned results, it is understood that the subchronic administration of cilostazol can significantly improve the condition of schizophrenia in the model animals. Therefore, it has become clear that the present invention comprising cilostazol or a pharmaceutical salt thereof is useful as a medicament for preventing and/or treating schizophrenia.

Example 2

Study with Model Animals for Schizophrenia

Dizocilpine (MK-801) which is an NMDA receptor antagonist causes symptoms closely similar to schizophrenia in human, and hence it is generally used to prepare model animals of schizophrenia. In this experiment, cilostazol was studied about the effect affecting the locomotion of mice which was enhanced by administering dizocilpine.

Male ddY mice (7-8 weeks old) were put in a scanning apparatus of spontaneous motor activity (SCANET SV-10, Melquest, Toyama, Japan). After 30 minutes, vehicle (0.3% CMC) or cilostazol (0.03, 0.1, 0.3, 1.0, and 3.0 mg/kg) was orally administered to the mice, and after additional 30 minutes dizocilpine (0.1 mg/kg) was administered subcutaneously. Then, the locomotion of the mice was measured for 2 hours.

Figure 2:
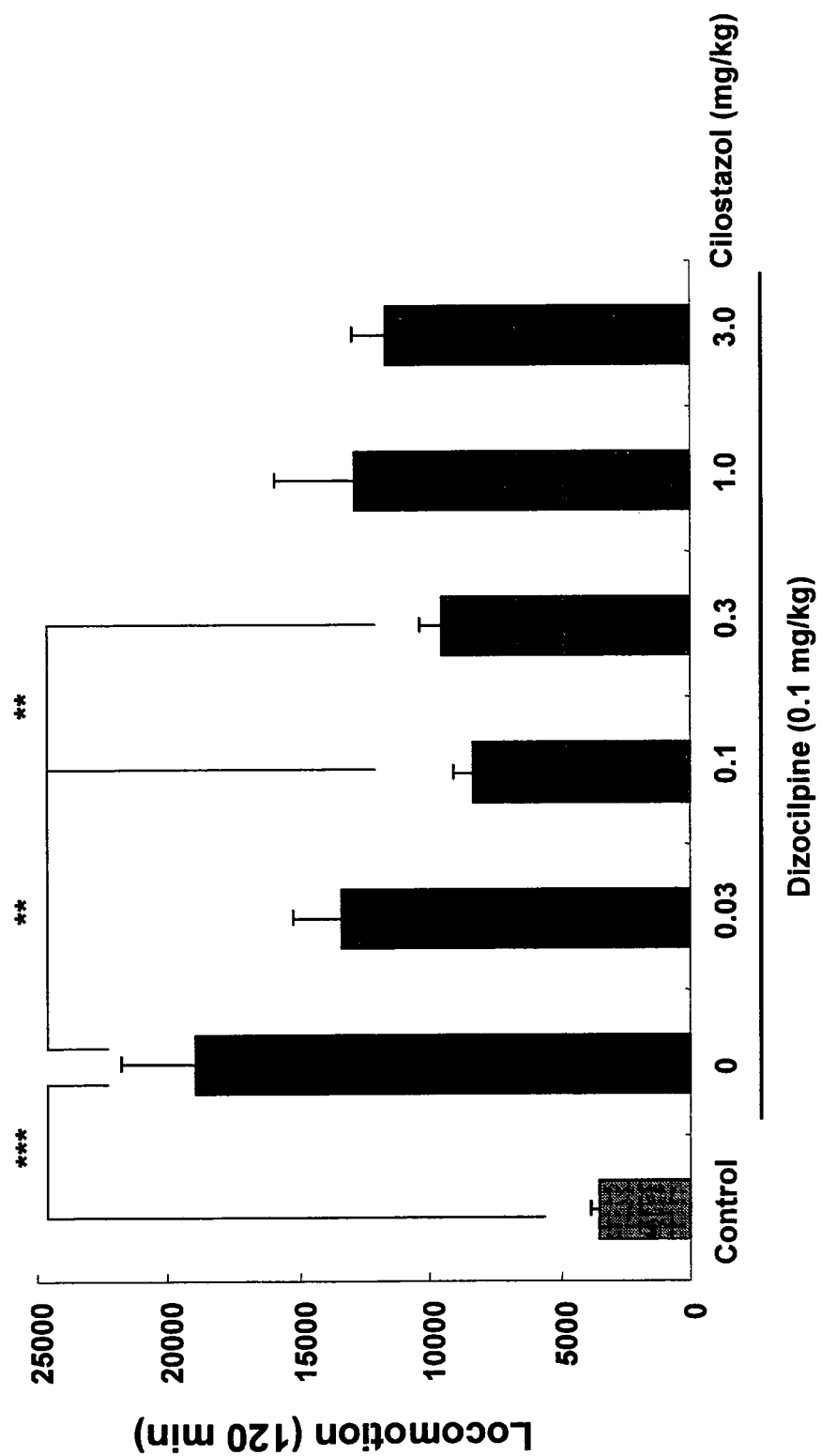
FIG. 2 shows the effects of cilostazol on dizocilpine-induced hyherlocomotion in mice.

As shown in FIG. 2, it has found that the locomotion enhanced by administering dizocilpine (0.1 mg/kg) was significantly inhibited by the pre-administration of cilostazol.

Example 3

Auditory Startle and Prepulse Inhibition of the Acoustic Startle Reflex (Behavior Related to Schizophrenia)

The test animals were prepared by similar means of the above Example 2. Cilostazol was administered one hour before testing.

Testing was conducted in eight startle devices each consisting of a Plexiglas cylinder (5 cm in diameter) mounted on a Plexiglas platform in a ventilated sound attenuated cubicle with a high-frequency loudspeaker producing all acoustic stimuli. The background noise of each chamber was 65 dB. Movements within the cylinder were detected and transduced by a piezoelectric accelerometer attached to the Plexiglas base and digitized and stored by a computer. Beginning at the stimulus onset, readings were recorded to obtain the animals' startle amplitude.

Each section was initiated with a 10 minutes acclimation period followed by six successive trials, which were not included in the analysis.

Procedure:

Startle pulse alone (ST110, 110 dB/40 msec); eight different prepulse trials in which either 20-msec-long 69, 73, 77, and 81 dB stimuli were presented alone (P69, P73, P77, P81) or preceded the 110 dB pulse by 100 msec (PP69, PP73, PP77, PP81); and finally one trial in which only the background noise was presented to measure the baseline movements in the cylinder.

All trials were presented in a pseudorandom order, and the average intertrial interval (ITI) was 15 msec. The startle data and percentage prepulse inhibition (PPI) were analyzed by MANOVA (two-ways ANOVA).

Figure 3:
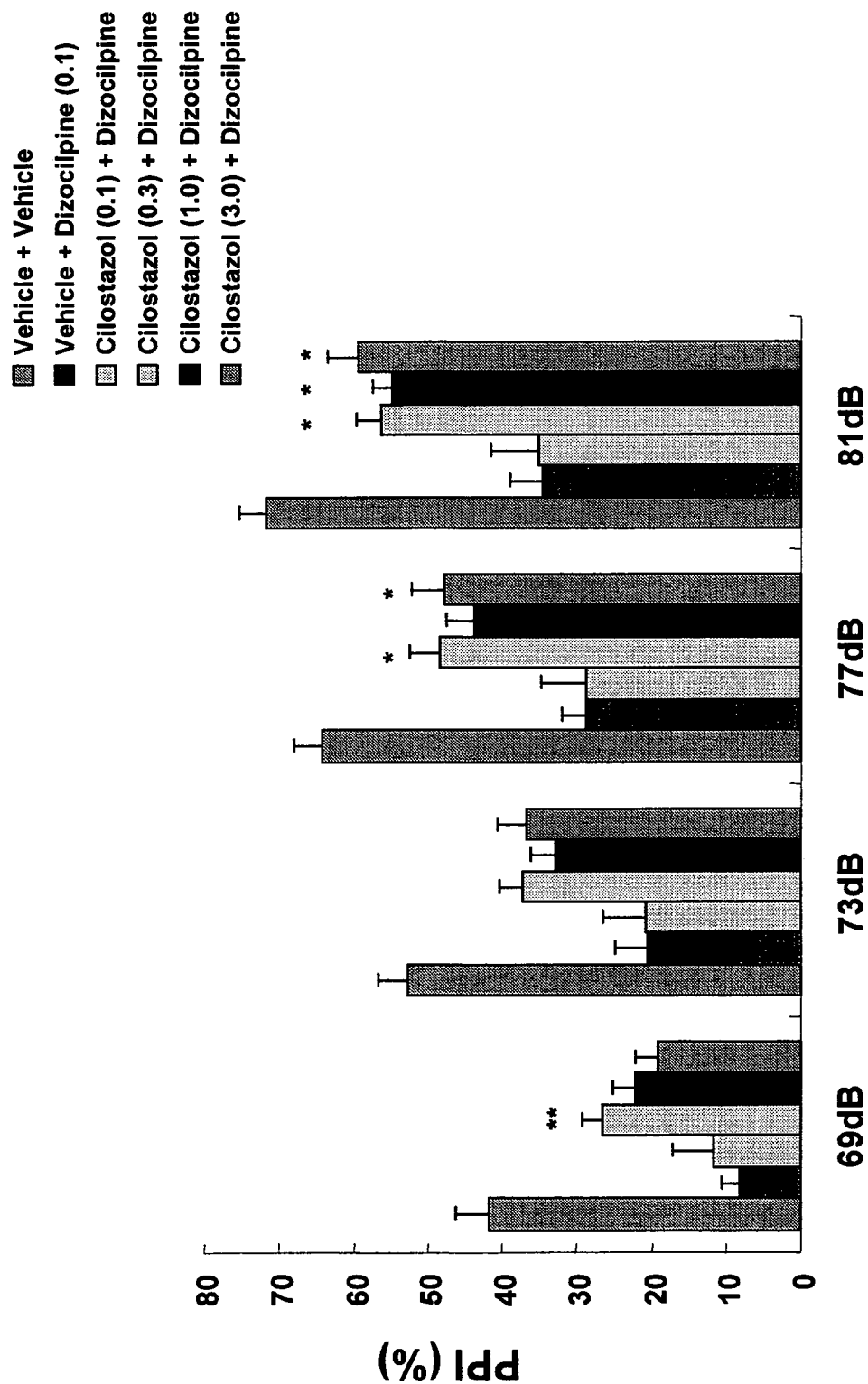
FIG. 3 shows the effects of cilostazol on dizocilpine-induced PPI deficits in mice.

As shown in FIG. 3, it has been found that PPI deficits caused by administration of dizocilpine (0.1 mg/kg) were significantly inhibited by the pre-administration of cilostazol, in a dose dependent manner.

INDUSTRIAL APPLICABILITY

As mentioned above, the present invention can be used as a medicament useful for schizophrenia.

The invention claimed is:

1. A method for treating schizophrenia which comprises administering as an active ingredient an effective amount of a carbostyril derivative or a salt thereof to a patient in need thereof of the general formula:

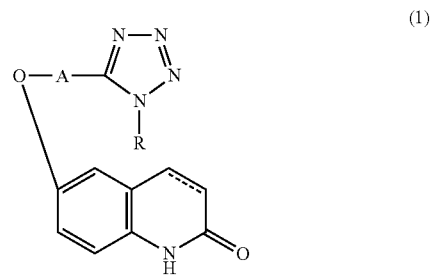

(1)

wherein A is a lower alkylene group, R is a cycloalkyl group, the bonding between 3- and 4-positions of the carbostyril skeleton is a single bond or a double bond, or a salt thereof.

2. The method of claim 1, wherein the active ingredient is 6-[4-(1-cyclohexyl-1H-tetrazol-5-yl)butoxy]3,4-dihydrocarbostyril or a salt thereof.

* * * * *

UNITED STATES PATENT AND TRADEMARK OFFICE
CERTIFICATE OF CORRECTION

| | | |
|---|---|---|
| PATENT NO. | : 8,431,606 B2 | Page 1 of 1 |
| APPLICATION NO. | : 12/593886 | |
| DATED | : April 30, 2013 | |
| INVENTOR(S) | : Hashimoto et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this
Twenty-sixth Day of July, 2016

Michelle K. Lee
*Director of the United States Patent and Trademark Office*